(12) United States Patent
Sawamura et al.

(10) Patent No.: US 11,499,947 B2
(45) Date of Patent: Nov. 15, 2022

(54) SAMPLE INTRODUCTION DEVICE

(71) Applicant: SHIMADZU CORPORATION, Kyoto (JP)

(72) Inventors: Isao Sawamura, Kyoto (JP); Akira Aono, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 613 days.

(21) Appl. No.: 16/470,392

(22) PCT Filed: Feb. 22, 2018

(86) PCT No.: PCT/JP2018/006352
§ 371 (c)(1),
(2) Date: Jun. 17, 2019

(87) PCT Pub. No.: WO2019/163039
PCT Pub. Date: Aug. 29, 2019

(65) Prior Publication Data
US 2021/0333246 A1  Oct. 28, 2021

(51) Int. Cl.
*G01N 30/12* (2006.01)
*G01N 30/02* (2006.01)

(52) U.S. Cl.
CPC ....... *G01N 30/12* (2013.01); *G01N 2030/025* (2013.01); *G01N 2030/128* (2013.01)

(58) Field of Classification Search
CPC ............. G01N 30/12; G01N 2030/025; G01N 2030/128
USPC ....................................................... 73/23.41
See application file for complete search history.

(56) References Cited

U.S. PATENT DOCUMENTS

| 4,418,040 A | 11/1983 | Karamian |
| 5,415,840 A | 5/1995 | Sano et al. |
| 5,985,215 A * | 11/1999 | Sakazume ............ G01N 35/026 422/65 |
| 6,170,556 B1 * | 1/2001 | Battagliarin ........... G01N 1/286 164/332 |

(Continued)

FOREIGN PATENT DOCUMENTS

| CN | 206756758 U | 12/2017 |
| JP | 3-110368 U | 11/1991 |
| JP | 6-130067 A | 5/1994 |

(Continued)

OTHER PUBLICATIONS

Notice of Reasons for Refusal dated Mar. 3, 2020 from the Japanese Patent Office in Application No. 2017-021515.

(Continued)

*Primary Examiner* — John Fitzgerald
*Assistant Examiner* — Rodney T Frank
(74) *Attorney, Agent, or Firm* — Sughrue Mion, PLLC

(57) ABSTRACT

A sample introduction device 10 includes a tube holding section 21 and a sample removing mechanism 40. The sample removing mechanism 40 removes a sample 6 in a sample tube 2 held by the tube holding section 21. Thus, in the sample introduction device 10, the sample 6 in the sample tube 2 held by the tube holding section 21 can be automatically removed. As a result, the operator no longer needs to perform an operation of taking out the sample 6 from the sample tube 2. Thus, a work load on the operator can be reduced.

10 Claims, 17 Drawing Sheets

(56) References Cited

U.S. PATENT DOCUMENTS

2018/0356316 A1* 12/2018 Aono .................. G01N 30/465

FOREIGN PATENT DOCUMENTS

| | | |
|---|---|---|
| JP | 2001-242150 A | 9/2001 |
| JP | 2004-125539 A | 4/2004 |
| JP | 2005-83892 A | 3/2005 |
| JP | 2007-225420 A | 9/2007 |
| JP | 2013-053974 A | 3/2013 |
| JP | 5648608 B2 | 1/2015 |

OTHER PUBLICATIONS

Written Opinion for PCT/JP2018/006352 dated May 29, 2018 [PCT/ISA/237].

Communication dated Aug. 20, 2021, from the China National Intellectual Property Administration in application No. 201880004815.3.

Communication dated Feb. 7, 2021 from the State Intellectual Property Office of the P.R. of China in Application No. 201880004815.3.

* cited by examiner

SAMPLE INTRODUCTION DEVICE

CROSS REFERENCE TO RELATED APPLICATIONS

This application is a National Stage of International Application No. PCT/JP2018/006352, filed on Feb. 22, 2018.

TECHNICAL FIELD

The present invention relates to a sample introduction device that heats a sample tube containing a sample to desorb a sample compound and introduces the sample compound into an analysis section.

BACKGROUND ART

Conventionally, sample introduction devices of a thermal desorption type have been used in a case of introducing an extremely small amount of sample compounds into an analysis section, such as a case where environmental pollutants in the air are analyzed (see, for example, Patent Document 1 listed below). The sample introduction device of this type heats a sample tube containing a sample, whereby sample compounds are desorbed to be temporarily trapped in a trap column. Then, the sample compounds in the trap column are heated to be desorbed, so that they can be introduced into the analysis section.

Such a sample introduction device may be used for measuring volatile organic compounds (VOCs) and semi volatile organic compounds (SVOCs) in a sample, for example. VOCs and SVOCs in a sample are measured as follows. First, a sample contained in a sample tube is heated up to 80 to 100° for extracting a VOC from the sample and carrier gas flows into the sample tube. As a result, the VOC extracted from the sample is sent out by the carrier gas to be introduced into the analysis section.

In this process, an SVOC is extracted from the sample together with the VOC. The SVOC is a high-boiling component, and thus adheres to an inner wall of the sample tube so as not to be introduced into the analysis section. Next, the sample is removed from the sample tube. Then, the resultant sample tube is heated up to 280 to 300°, whereby the SVOC in the sample tube is diffused. Then, the carrier gas further flows into the sample tube, whereby the SVOC is sent out from the sample tube to be introduced into the analysis section. In this manner, the VOC and the SVOC in the sample are measured by heating the sample tube at a relatively low temperature, then removing the sample from the sample tube, and then heating the sample tube at a high temperature.

PRIOR ART DOCUMENT

Patent Document

Patent Document 1: Japanese Patent No. 5,648,608

SUMMARY OF THE INVENTION

Problems to be Solved by the Invention

When measuring VOCs and SVOCs in a sample using the conventional sample introduction device, the sample is manually removed from the sample tube. Thus, there have been drawbacks that an operator is required to go through a cumbersome operation and that a long period of time is required for the measurement. Such drawbacks similarly arise in a case where a sample is removed from a sample tube in another operation using the sample introduction device.

The present invention is made in view of the above, and an object of the present invention is to provide a sample introduction device that can reduce a work load on an operator.

Means for Solving the Problems (1) A sample introduction device according to the present invention heats a sample tube containing a sample to desorb a sample compound and introduce the sample compound into an analysis section. The sample introduction device includes a tube holding section and a sample removing mechanism. The tube holding section holds the sample tube. The sample removing mechanism removes the sample in the sample tube held by the tube holding section.

With this configuration, the sample in the sample tube held by the tube holding section can be automatically removed by the sample removing mechanism.

Thus, the operator no longer needs to perform an operation of taking out the sample from the sample tube.

As a result, a work load on the operator can be reduced. Furthermore, the time required for a series of processing in the sample introduction device can be shortened.

(2) The sample removing mechanism may include a shaft. The shaft is inserted into the sample tube to push out the sample.

With this configuration, the sample in the sample tube can be removed with a simple configuration.

(3) The shaft may include a shaft section and a contact section. The shaft section slides in an axial direction. The contact section has an outer diameter, about an axis, larger than an outer diameter of the shaft section, and comes into contact with the sample in the sample tube.

With this configuration, the contact section comes into contact with the sample when the shaft is inserted in the sample tube. When the shaft is further inserted into the sample tube, the contact section pushes out the sample from the sample tube.

Thus, the portion of the sample removing mechanism that comes into contact with the sample in the process of removing the sample can be limited to the contact section.

(4) The contact section may be detachably attached to the shaft section.

With this configuration, the contact section can be exchanged and maintained easily.

(5) The contact section may be provided with a tapered surface that is tapered toward a distal end.

With this configuration, the contact section is inserted into the sample tube from a tapered portion of the contact section.

This enables the contact section to be easily inserted into the sample tube.

(6) The sample introduction device may further include a shaft heating section. The shaft heating section heats the shaft that has been pulled out from the sample tube.

With this configuration, when the shaft is inserted into the sample tube and the sample compound remaining in the sample tube adheres to the shaft, the shaft heating section heats the shaft, so that the adhered sample compound can be diffused (dispersed).

Thus, when the shaft is continuously used, the shaft having the adhered sample compound can be prevented from being inserted into the sample tube.

As a result, occurrence of so-called cross contamination can be prevented, that is, the sample component adhered to the shaft can be prevented from mixing into the sample tube to adversely affect the subsequent analysis and the like.

(7) The sample introduction device may further include a purge gas supply section. The purge gas supply section blows purge gas onto an outer circumference surface of the shaft heated by the shaft heating section.

With this configuration, the purge gas is blown onto the outer circumference surface of the shaft from the purge gas supply section, whereby the sample compound diffused from the surface of the shaft can be moved away from the shaft.

Thus, the occurrence of the cross contamination can more effectively be prevented.

(8) The sample introduction device may further include an extrusion gas supply section. The extrusion gas supply section supplies extrusion gas into the shaft to cause the extrusion gas to be ejected from a distal end of the shaft toward the sample in the sample tube.

With this configuration, when the shaft is inserted into the sample tube, the extrusion gas ejected from the extrusion gas supply section can push out the sample in the sample tube.

Thus, the sample in the sample tube can be smoothly pushed out.

(9) The sample introduction device may further include a sample detection section. The sample detection section detects presence or absence of the sample in the sample tube after the sample removing mechanism has been operated.

With this configuration, whether the sample in the sample tube has been pushed out can be confirmed based on the detection by the sample detection section.

Effects of the Invention

According to the present invention, the sample in the sample tube held by the tube holding section can be automatically removed by the sample removing mechanism. Thus, the operator no longer needs to perform an operation of taking out the sample from the sample tube. As a result, a work load on the operator can be reduced.

MODE FOR CARRYING OUT THE INVENTION

1. Configuration of Sample Introduction Device

Figure 1:
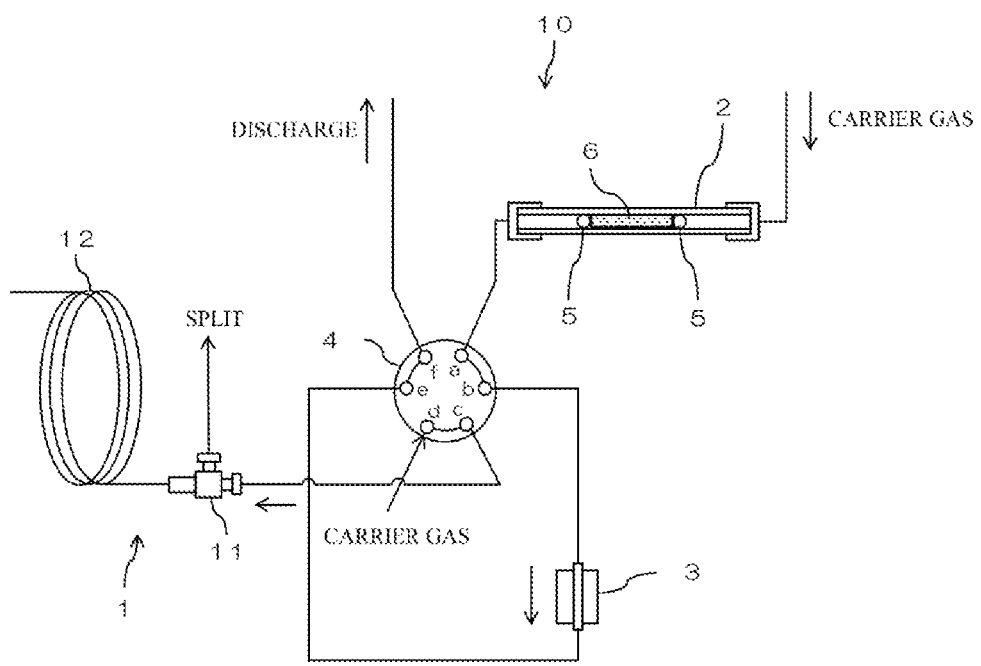
FIG. 1 is a flow path diagram illustrating an example of a configuration of a sample introduction device according to a first embodiment of the present invention.

FIG. 1 is a flow path diagram illustrating an example of a configuration of a sample introduction device according to a first embodiment of the present invention.

The sample introduction device 10 is a sample introduction device for a gas chromatograph, which is for introducing a sample into a gas chromatograph 1. A sample tube 2 in which a sample is sealed is set to the sample introduction device 10, and sample gas generated as a result of vaporization in the sample tube 2 is introduced into the gas chromatograph 1. The gas chromatograph 1 is a concept including a gas chromatograph mass spectrometer.

The sample introduction device 10 includes a trap section 3, a flow path switching section 4, and the like. The trap section 3 is connected to the flow path switching section 4 through a pipe.

The sample tube 2 is a thin elongated transparent or semitransparent tubular member made of quartz for example, and is set to the sample introduction device 10 to be a part of a pipe in communication with the flow path switching section 4.

A sample 6 is sandwiched between a pair of silica wool members 5 to be held in the sample tube 2. The sample 6 is a solid sample such as resin for example, but this should not be construed in a limiting sense, and may also be a liquid such as an adhesive for example. Carrier gas is supplied into the sample tube 2 through a pipe, and passes through the pair of silica wool members 5 to be sent to the flow path switching section 4. This carrier gas may be inert gas such as nitrogen gas or helium gas, or may be active gas.

In the trap section 3 including a trap column for example, the sample (sample gas) generated as a result of vaporization in the sample tube 2 is trapped and concentrated. When the trap section 3 with the concentrated sample is heated, the sample in the trap section 3 volatilizes to be desorbed, and the resultant sample is supplied to the gas chromatograph 1 by means of the carrier gas.

For example, the flow path switching section 4 is formed by a six-way valve including six ports a to f. The port a of the flow path switching section 4 is in communication with the internal space of the sample tube 2 set to the sample introduction device 10. The trap section 3 has both end portions in communication with the respective ports b and e of the flow path switching section 4. The port c of the flow path switching section 4 is in communication with the gas chromatograph 1. Carrier gas is supplied to the port d of the flow path switching section 4. This carrier gas is inert gas such as nitrogen gas or helium gas. The port f of the flow path switching section 4 is in communication with a discharge port.

The gas chromatograph 1 includes a sample introduction section 11, a column 12, and the like. The sample, which is supplied from the trap section 3 to the gas chromatograph 1 together with the carrier gas, is introduced into the column 12 from the sample introduction section 11 and is separated into sample compounds while passing through the column 12. The sample compounds thus separated are detected by a detector (not illustrated), and a chromatogram is obtained as an analysis result.

In this example, the sample is introduced into the column 12 by so-called split introduction. Specifically, the sample supplied from the trap section 3 to the sample introduction section 11 is partially discharged to the outside together with the carrier gas. Note that this configuration should not be construed in a limiting sense, and the sample supplied from the trap section 3 to the sample introduction section 11 may be entirely introduced into the column 12.

In the state illustrated in FIG. 1, the flow path switching section 4 has the ports a and b communicating with each other, and the ports e and f communicating with each other. Thus, the carrier gas supplied to the sample tube 2 from one end side (upstream side) flows into the trap section 3 via the flow path switching section 4, after passing through the sample tube 2. When the sample tube 2 is heated from the outside, predetermined gas (sample gas) is extracted from the sample 6 contained therein, as described later. The sample gas generated in the sample tube 2 is sent to the flow path switching section 4 together with the carrier gas supplied into the sample tube 2. The sample gas is supplied toward the gas chromatograph 1 by means of the carrier gas, to be trapped in the trap section 3. After the sample is trapped in the trap section 3, the carrier gas is discharged from the discharge port through the flow path switching section 4.

In the state illustrated in FIG. 1, the flow path switching section 4 has the ports c and d communicating with each other. Thus, the carrier gas supplied to the port d of the flow path switching section 4 is introduced into the gas chromatograph 1 through the port c without passing through the trap section 3.

Figure 2:
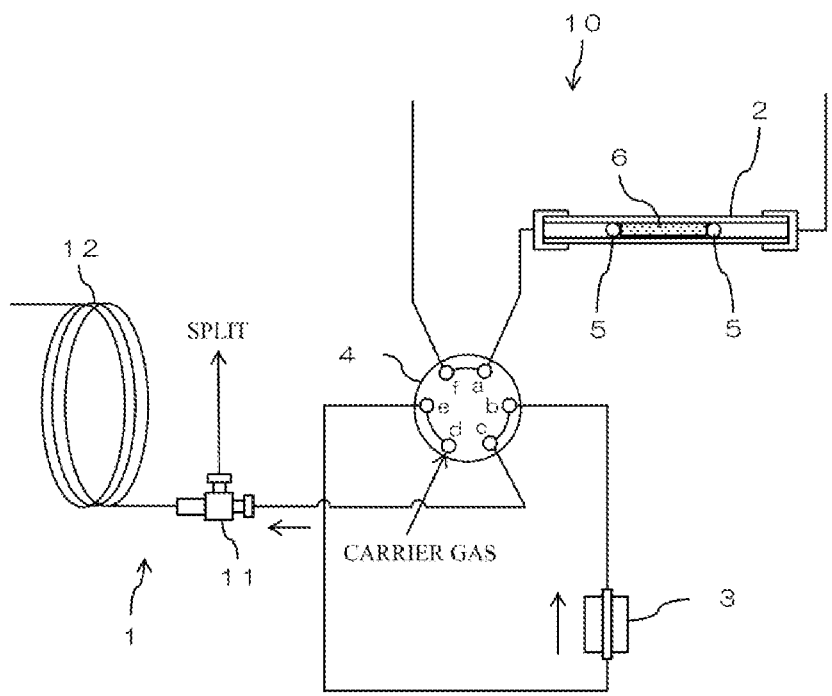
FIG. 2 is a flow path diagram illustrating a state where a flow path switching section is switched from the state illustrated in FIG. 1.

FIG. 2 is a flow path diagram illustrating a state where the flow path switching section 4 is switched from the state illustrated in FIG. 1. In this state, the flow path switching section 4 has the ports b and c communicating with each other, and the ports d and e communicating with each other. Thus, the carrier gas supplied to the port d of the flow path switching section 4 flows into the trap section 3 through the port e. At this point, the trap section 3 is heated. Thus, the sample concentrated in the trap section 3 is desorbed, and is then supplied toward the gas chromatograph 1 through the ports b and c of the flow path switching section 4. In the state illustrated in FIG. 2, the flow path switching section 4 has the ports a and f communicating with each other.

As described above, in the sample introduction device 10, the sample tube 2 that contains the sample is heated and the carrier gas flows into the sample tube 2, whereby the sample gas as a result of extraction (desorption) in the sample tube 2 is trapped in the trap section 3. After the sample is trapped in the trap section 3, the flow path switching section 4 is switched. Then, the trap section 3 is heated and the carrier gas flows into the trap section 3, whereby the sample is introduced from the trap section 3 to the gas chromatograph 1.

Figure 3:
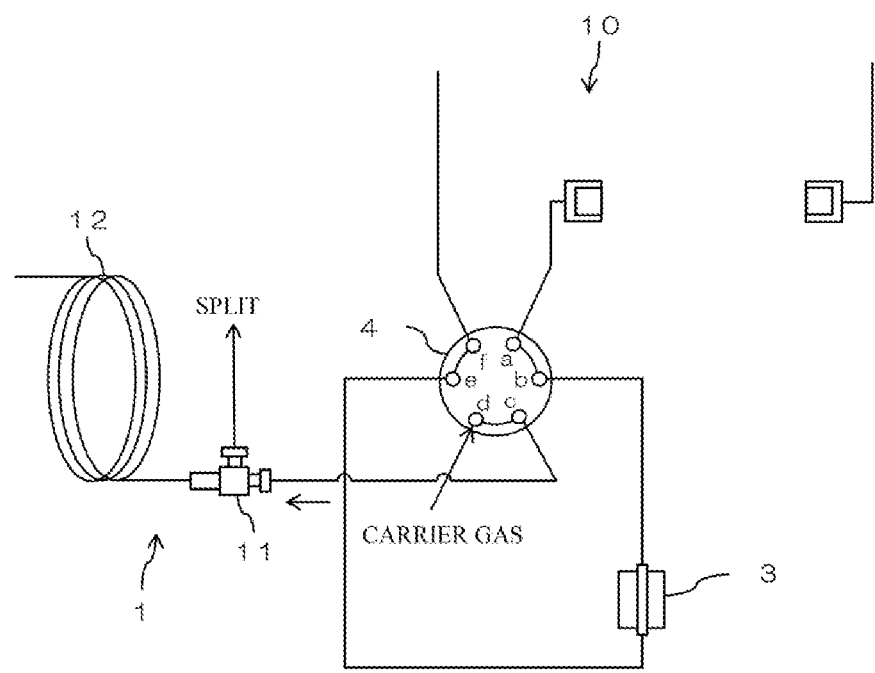
FIG. 3 is a flow path diagram illustrating a state where the flow path switching section is switched from the state illustrated in FIG. 2 and the sample tube is moved.

In the sample introduction device 10, the sample tube 2 can be moved as appropriate, as described later. FIG. 3 is a flow path diagram illustrating a state where the flow path switching section is switched from the state illustrated in FIG. 2 and the sample tube 2 is moved.

As will be described in detail later, the sample introduction device 10 has a configuration for moving the sample tube 2 and for executing various types of processing on the sample tube 2. FIG. 3 illustrates a state where, in the sample introduction device 10, the sample tube 2 is moved for performing sample removal processing (described later) on the sample tube 2. The flow path switching section 4 in FIG. 3 forms the flow path in the same state as the state illustrated in FIG. 1. In this state, the carrier gas supplied to the port d of the flow path switching section 4 is introduced into the gas chromatograph 1 through the port c. Thus, in the sample introduction device 10, the carrier gas is introduced into the gas chromatograph 1 without passing through the trap section 3, while the sample removal processing on the sample tube 2 is being executed.

2. Configuration of Heating Mechanism

Figure 4A:
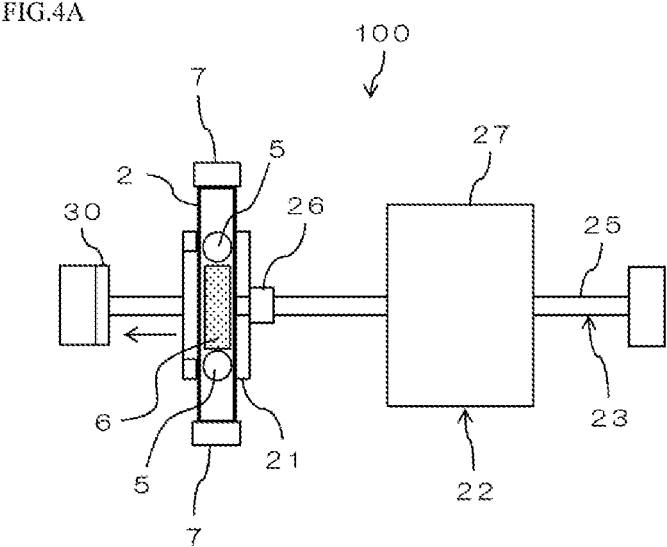
FIG. 4A is a plan view illustrating an example of a configuration of a heating mechanism for the sample tube in the sample introduction device, in a state where the sample tube is at an initial position.
Figure 4B:
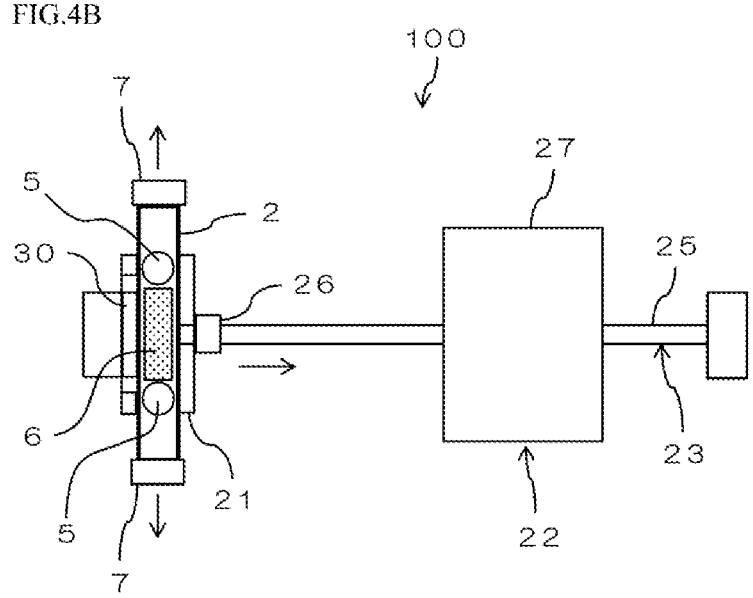
FIG. 4B is a plan view illustrating an example of a configuration of the heating mechanism for the sample tube in the sample introduction device, in a state where the sample tube is in contact with a pressing section.
Figure 4C:
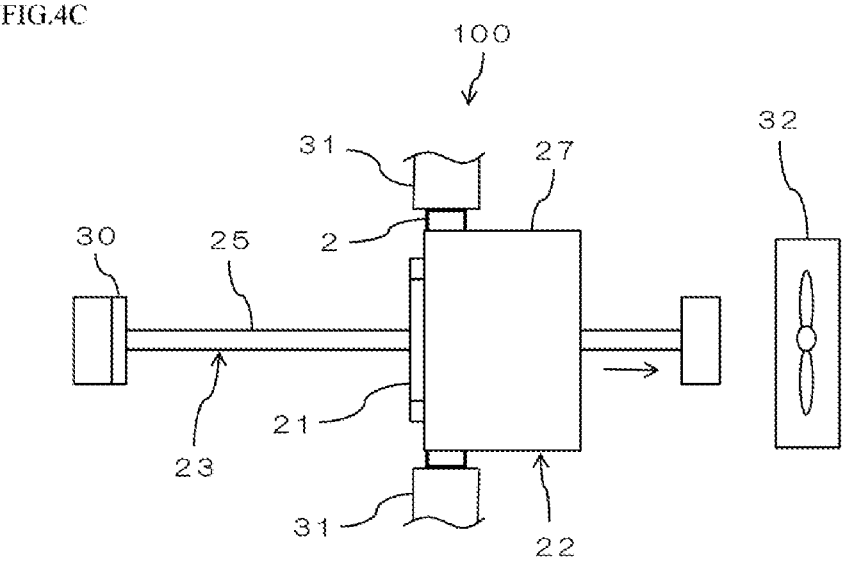
FIG. 4C is a plan view illustrating an example of a configuration of the heating mechanism for the sample tube in the sample introduction device, in a state where the sample tube is heated by the heating mechanism.
Figure 4D:
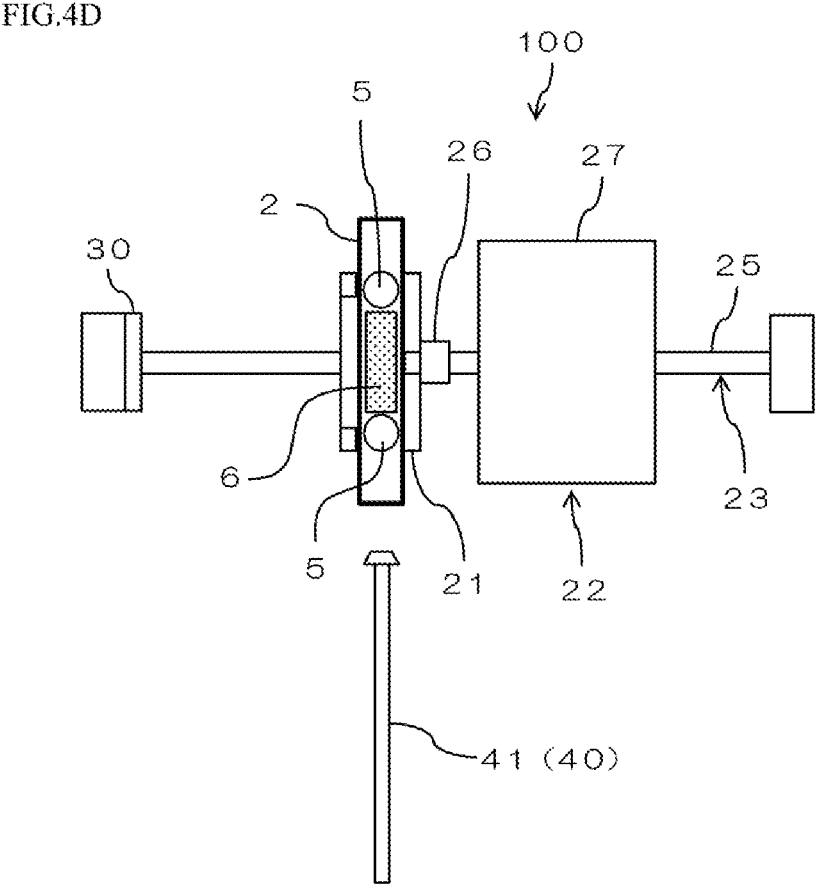
FIG. 4D is a plan view illustrating an example of a configuration of the heating mechanism for the sample tube in the sample introduction device, in a state where the sample tube is at a removal position.
Figure 4E:
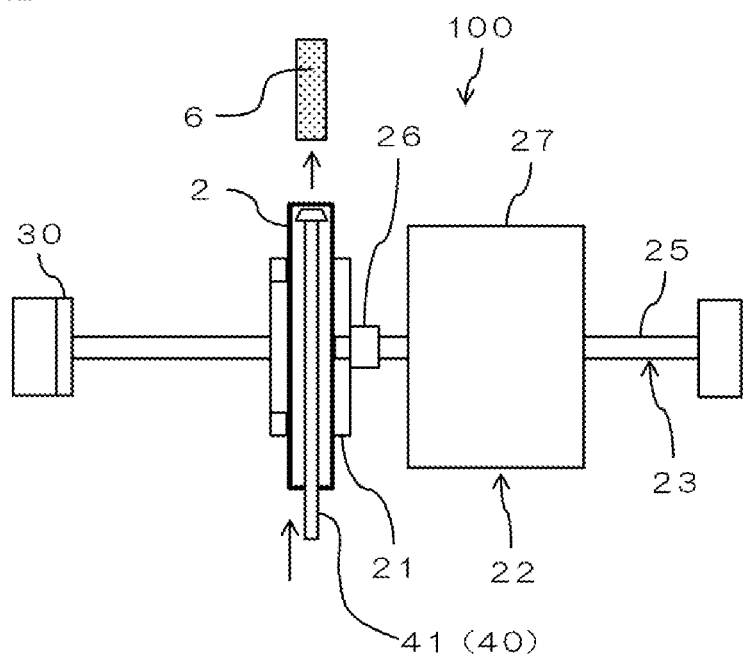
FIG. 4E is a plan view illustrating an example of a configuration of the heating mechanism for the sample tube in the sample introduction device, in a state where the sample has been removed by insertion of a shaft in the sample tube.
Figure 4F:
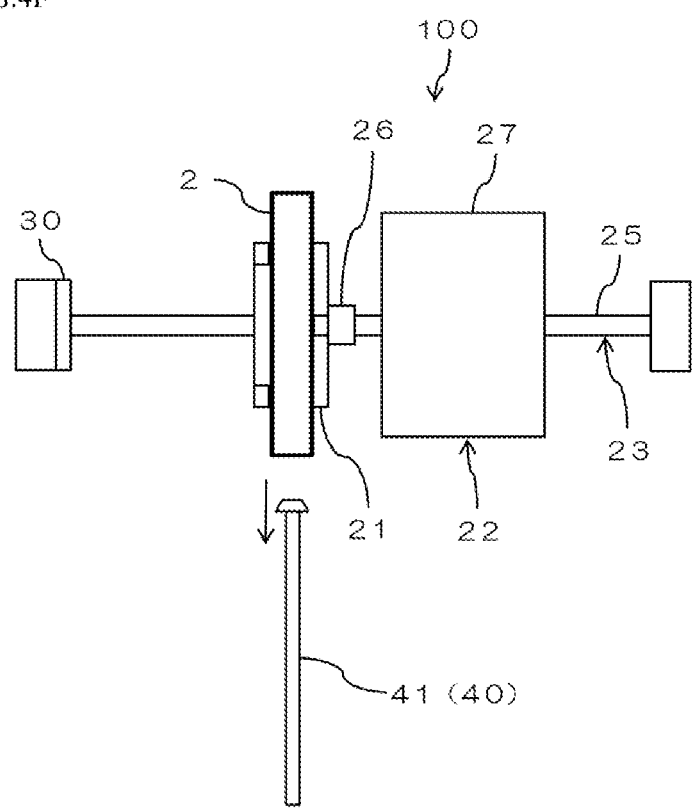
FIG. 4F is a plan view illustrating an example of a configuration of the heating mechanism for the sample tube in the sample introduction device, in a state where the shaft has been pulled out from the sample tube.

FIG. 4A to FIG. 4F are plan views each illustrating an example of a configuration of a heating mechanism 100 for the sample tube 2 in the sample introduction device 10. Specifically, FIG. 4A illustrates a state where the sample tube 2 is at an initial position. FIG. 4B illustrates a state where the sample tube 2 is in contact with a pressing section 30. FIG. 4C illustrates a state where the sample tube 2 is heated by the heating mechanism 100. FIG. 4D illustrates a state where the sample tube 2 is at a removal position. FIG. 4E illustrates a state where the sample has been removed by insertion of a shaft 41 in the sample tube 2. FIG. 4F illustrates a state where the shaft 41 has been pulled out from the sample tube 2. FIG. 5A to FIG. 5F are side views of the heating mechanism 100 respectively corresponding to FIG. 4A to FIG. 4F.

As illustrated in FIG. 4A, before the analysis, the sample tube 2 containing the sample 6 has both end portions closed by caps 7. As described above, the sample 6 is sandwiched between the pair of silica wool members 5 to be held in the sample tube 2. The heating mechanism 100 includes a tube holding section 21 that holds the sample tube 2, a tube heating section 22 that heats the sample tube 2, and a movement mechanism 23.

The movement mechanism 23 includes a rotatable support shaft 25 that linearly extends along a horizontal direction, and a nut 26 attached to the support shaft 25. The support shaft 25 has an outer circumference surface with a thread, and the nut 26 is screwed onto the thread to be attached to the support shaft 25. The sample tube 2 is held by the tube holding section 21 to extend in a horizontal direction that is orthogonal to the support shaft 25. The nut 26 is fixed to the tube holding section 21. Thus, rotation of the support shaft 25 causes movement of the tube holding section 21 along the support shaft 25 in a direction depending on a direction of the rotation.

The tube heating section 22 is formed to have a configuration in which a heater block 27 and a supporting table 28 supporting the heater block 27 are integrated, and is disposed with the support shaft 25 passing through the supporting table 28. Note that the support shaft 25 simply passes through the supporting table 28, that is, not screwed into the supporting table 28, and thus the rotation of the support shaft 25 does not cause the tube heating section 22 to move like the tube holding section 21. Thus, when the support shaft 25 is rotated in one direction, the tube holding section 21 can be moved toward the tube heating section 22, and when the support shaft 25 is rotated in the other direction, the tube holding section 21 can be moved away from the tube heating section 22.

Figure 5A:
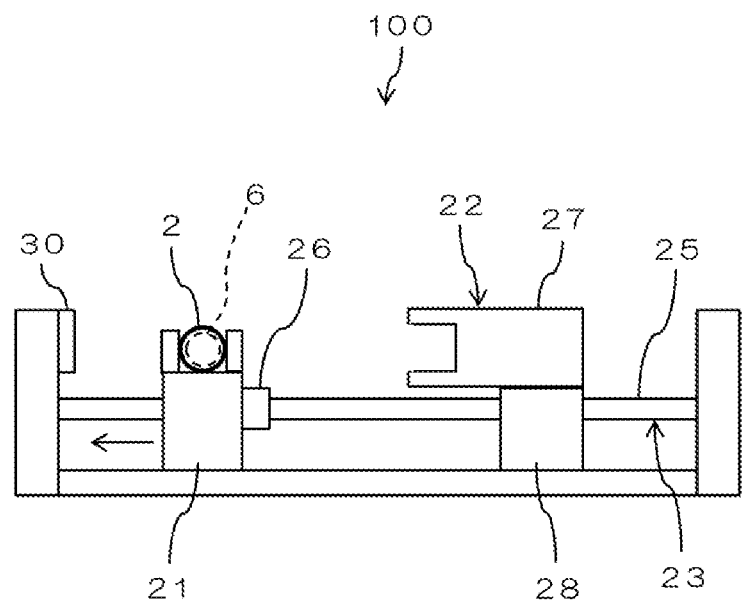
FIG. 5A is a side view of the heating mechanism corresponding to FIG. 4A.

The pressing section 30 for pressing and sandwiching the sample tube 2 held by the tube holding section 21 is provided on a side opposite to the tube heating section 22, relative to the tube holding section 21. When the sample tube 2 is set to the tube holding section 21 in a state where the tube holding section 21 is at the initial position as illustrated in FIG. 4A and FIG. 5A, the support shaft 25 is first rotated to move the tube holding section 21 toward the pressing section 30.

Figure 5B:
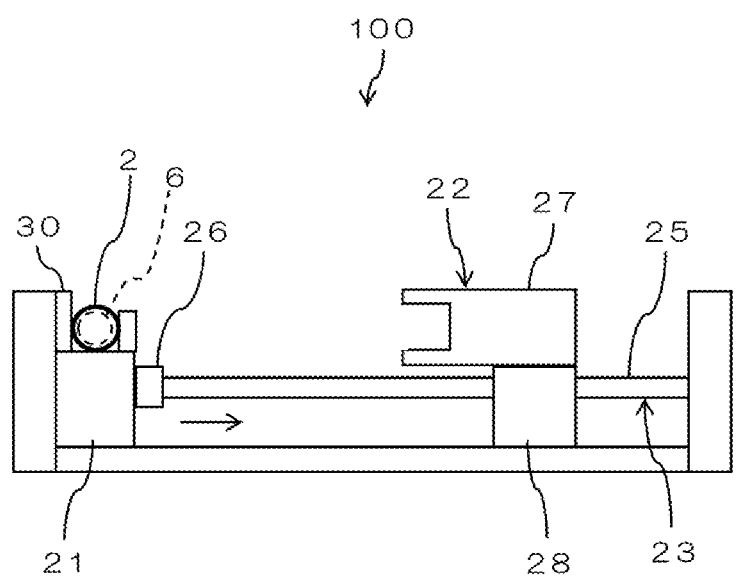
FIG. 5B is a side view of the heating mechanism corresponding to FIG. 4B.

As a result, the tube holding section 21 and the sample tube 2 are positioned at a pressed position as illustrated in FIG. 4B and FIG. 5B, with the sample tube 2 sandwiched between the tube holding section 21 and the pressing section 30 in contact with an outer circumference surface of the sample tube 2. A grip (not illustrated) is operated in this state to remove the caps 7 from both ends of the sample tube 2. In this process, the pressing section 30 applies pressing force so that the sample tube 2 can be prevented from moving in a lengthwise direction.

Figure 5C:
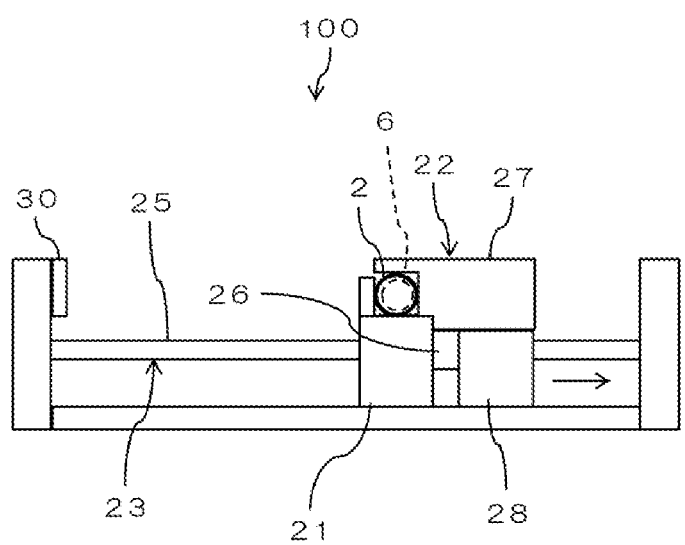
FIG. 5C is a side view of the heating mechanism corresponding to FIG. 4C.

Then, the support shaft 25 is rotated, whereby the tube holding section 21 moves toward the tube heating section 22 as illustrated in FIG. 4C and FIG. 5C. The sample tube 2 is in contact with the heater block 27 when the nut 26 comes into contact with the supporting table 28 of the tube heating section 22 and stops. Pipes 31 for causing the carrier gas to flow through the sample tube 2 are connected to both end portions of the sample tube 2 at this position (heating position).

In this state, the heater block 27 is heated, and the carrier gas flows through the pipes 31 to flow through the sample tube 2. As a result, a predetermined compound (sample compound) vaporizes to be desorbed from the sample 6 in the sample tube 2, and the sample compound is sent out from the sample tube 2 by means of the carrier gas to be trapped in the trap section 3. FIG. 1 illustrates the sample tube 2 in this state.

In this example, the inside of the sample tube 2 is heated up to 80 to 100°. A VOC is extracted as the sample gas from the sample 6 to be trapped in the trap section 3. In this process, an SVOC is also extracted from the sample 6, but the SVOC adheres to the inner wall of the sample tube 2 to remain in the sample tube 2.

Then, a cooling fan 32 operates to cool the heater block 27 and the sample tube 2. After the sample tube 2 has been sufficiently cooled, the trap section 3 is heated and the carrier gas is supplied into the trap section 3 as described above (see FIG. 2). Thus, the sample compound in the trap section 3 vaporizes to be desorbed, and the sample compound is introduced into the gas chromatograph 1 by means of the carrier gas.

Figure 5D:
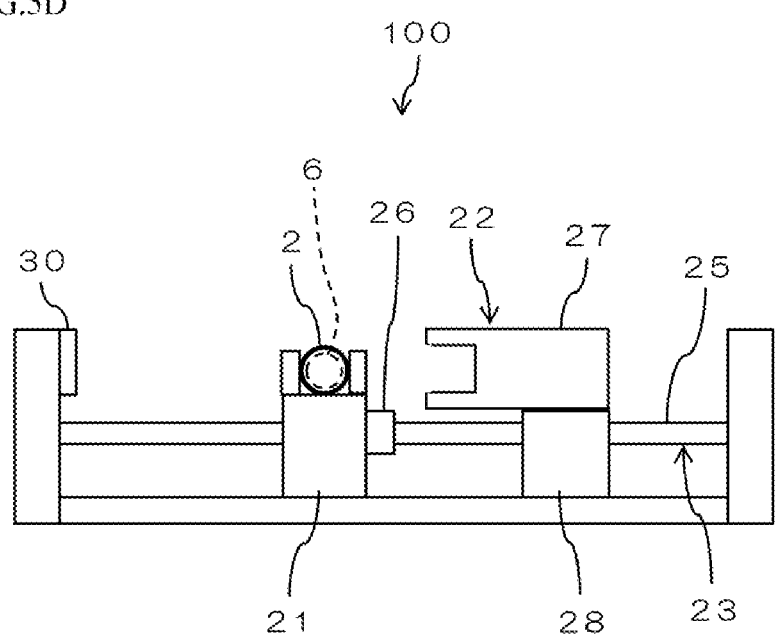
FIG. 5D is a side view of the heating mechanism corresponding to FIG. 4D.

Next, the pipes 31 are separated from both end portions of the sample tube 2 and the support shaft 25 rotates, whereby the tube holding section 21 moves toward the pressing section 30 as illustrated in FIG. 4D and FIG. 5D. The position of the tube holding section 21 and the sample tube 2 illustrated in FIG. 4D and FIG. 5D is the removal position. The removal position of the tube holding section 21 and the sample tube 2 is between the initial position illustrated in FIG. 4A and FIG. 5A and the heated position illustrated in FIG. 4C and FIG. 5C.

Figure 5E:
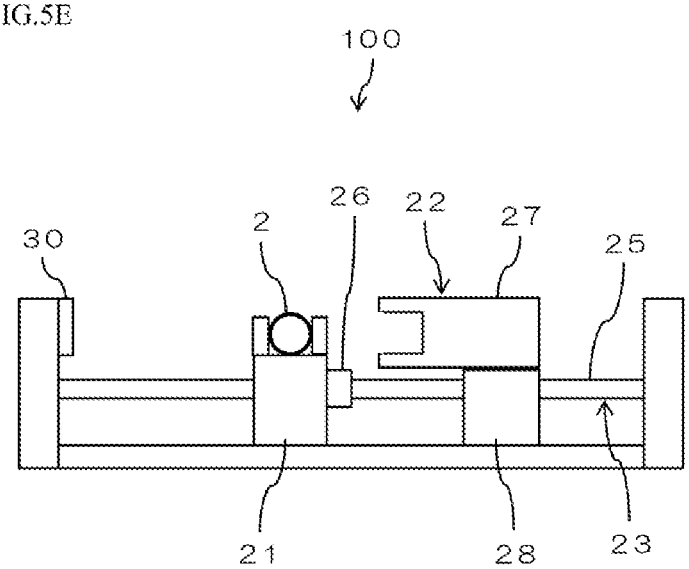
FIG. 5E is a side view of the heating mechanism corresponding to FIG. 4E.

In this state, the sample removing mechanism 40 removes the sample 6 (the silica wool members 5 and the sample 6) in the sample tube 2. As will be described in detail later, in the sample introduction device 10, the sample removing mechanism 40 includes a shaft 41. As illustrated in FIG. 4E and FIG. 5E, the shaft 41 is inserted into the sample tube 2 at the removal position to push out the sample 6 from the sample tube 2.

In this example, the sample 6 pushed out from the sample tube 2 is discarded, but may be collected and recycled.

Figure 5F:
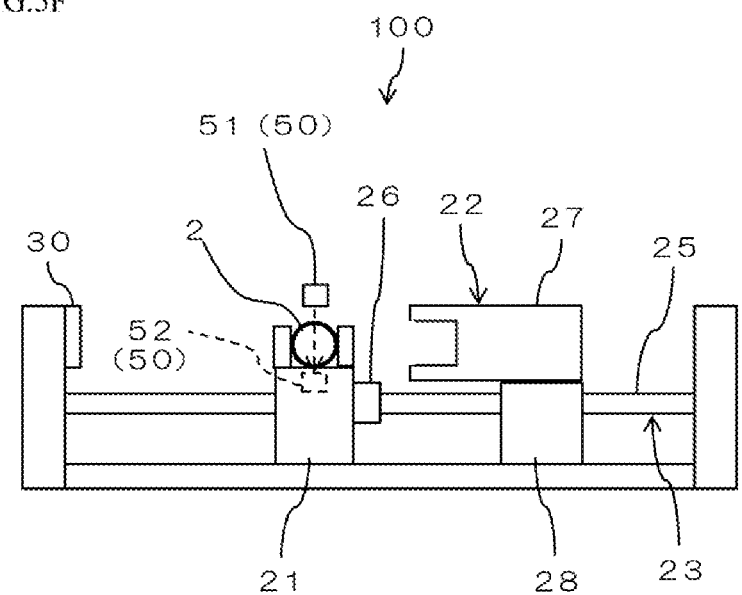
FIG. 5F is a side view of the heating mechanism corresponding to FIG. 4F.

Then, as illustrated in FIG. 4F and FIG. 5F, the shaft 41 is pulled out from the sample tube 2. The sample introduction device 10 includes a sample detection section 50. The sample detection section 50 detects a sample in the sample tube 2 at the removal position and includes a photointerrupter for example. Specifically, the sample detection section 50 includes a light emitting section 51 that emits light and a light receiving section 52 that receives light from the light emitting section 51. The light receiving section 52 is provided to the tube holding section 21. The light emitting section 51 is disposed above the light receiving section 52 with a gap therebetween. The sample tube 2 at the removal position is positioned between the light emitting section 51 and the light receiving section 52. In a state where the sample tube 2 is at the removal position, the sample detection section 50 detects that the sample 6 remains in the sample tube 2 when the light receiving section 52 does not receive light with an intensity equal to or higher than a threshold from the light emitting section 51, and detects that the sample 6 has been removed from the sample tube 2 when the light receiving section 52 receives light with an intensity equal to or higher than the threshold from the light emitting section 51.

When the sample detection section 50 detects that the sample 6 has been removed from the sample tube 2, the support shaft 25 rotates, whereby the tube holding section 21 returns to the initial position illustrated in FIG. 4A and FIG. 5A. Then, the sample tube 2 is collected from the tube holding section 21. Thereafter, the operation described above (the operation in FIG. 4A to FIG. 4F and FIG. 5A to FIG. 5F) is repeated to be performed one by one on a plurality of sample tubes 2. Then, the plurality of sample tubes 2 are temporarily automatically collected.

Then, the collected sample tubes 2 are automatically set to the tube holding section 21 one by one, and then each sample tube 2 is moved to the heated position due to the rotation of the support shaft 25. Then, similar to the processing in FIG. 4C and FIG. 5C, the heater block 27 is heated and the carrier gas flows through the pipes 31 to flow through the sample tube 2. As a result, the predetermined compound (sample compound) adhered to (remaining in) the sample tube 2 vaporizes to be desorbed, and is then sent out from the sample tube 2 by means of the carrier gas to be trapped in the trap section 3. The sample compound trapped in the trap section 3 is introduced into the gas chromatograph 1 as in the processing described above. Such processing is sequentially executed on the plurality of collected sample tubes 2.

In this example, the inside of the sample tube 2 is heated up to 280 to 300°, for example, by the heater block 27. Then, the SVOC remaining in the sample tube 2 is diffused, and the SVOC is trapped in the trap section 3.

In this example, as described above, the sample tube 2 is temporarily collected after having the sample removed, and the processing is sequentially executed on the plurality of collected sample tubes 2. Alternatively, the sample tube 2 after having the sample removed may not be collected, and may be directly heated again by the tube heating section 22.

3. Configuration of Sample Removing Mechanism

Figure 6:
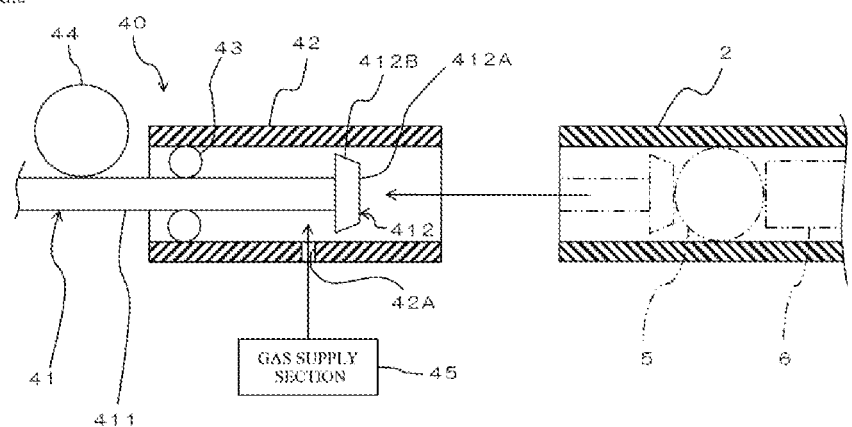
FIG. 6 is a schematic view illustrating a configuration of a sample removing mechanism.

FIG. 6 is a schematic view illustrating a configuration of a sample removing mechanism.

The sample removing mechanism 40 includes the shaft 41 described above, as well as a heater block 42, an O ring 43, a gear 44, and a gas supply section 45.

For example, the shaft 41 is made of a metal material and is formed to have an elongated rod shape. Inactivation processing is performed on the surface of the shaft 41. The shaft 41 includes a shaft section 411 and a contact section 412.

The shaft section 411 is formed to have a linearly extending elongated rod shape. Although not illustrated, a rack gear is formed on a circumference surface of the shaft section 411. For example, the shaft section 411 is held by a rail or the like, for example, to be movable (slidable) along the axial direction (lengthwise direction).

The contact section 412 is attached to a distal end of the shaft section 411. The contact section 412 is formed to have a disc shape tapered toward one side in the axial direction. The contact section 412 is detachably attached to the shaft section 411, while having the axis matching the axis of the shaft section 411. The contact section 412 has a distal end surface (surface on one side in the axial direction) serving as a contact surface 412A, and has a side surface (surface extending in a circumference direction about the axis) serving as a tapered surface 412B. The contact surface 412A is formed along a plane orthogonal to the axial direction. The tapered surface 412 is formed to be tapered toward the contact surface 412A. The contact section 412 has an outer diameter, about the axis, larger than the outer diameter of the shaft section 411.

The heater block 42 is positioned to face the sample tube 2 along the axial direction, in a state where the sample tube 2 is at the removal position. The heater block 42 is formed to have a cylindrical shape. The heater block 42 has a circumference surface with an opening 42A formed at the center. The shaft 41 is partially inserted in the heater block 42. The heater block 42 has an inner diameter larger than the outer diameter of the contact section 412 of the shaft 41. The shaft 41 is disposed in the heater block 42, while having the axial direction matching the axial direction of the heater block 42. The heater block 42 is an example of the shaft heating section.

The O ring 43 is disposed more on an inner side than an end portion of the heater block 42. Specifically, the O ring 43 is disposed more on the inner side than the end portion of the heater block 42 that is on a side opposite to the side facing the sample tube 2. The shaft section 411 of the shaft 41 is inserted in the O ring 43. Thus, the O ring 43 seals between the inner surface of the heater block 42 and the shaft section 411 of the shaft 41.

The gear 44 is in contact with the circumference surface of the shaft section 411 of the shaft 41, at a position separated from the heater block 42. Specifically, the gear 44 is a pinion gear that engages with the rack gear on the circumference surface of the shaft section 411 of the shaft 41. The gear 44 is rotatable about an orthogonal direction orthogonal to the axial direction, and rotates upon receiving driving force from a driving section (not illustrated).

The gas supply section 45 is configured to supply gas into the heater block 42 through the opening 42A. In this example, the gas supply section 45 supplies inert gas at 280 to 300°, for example, into the heater block 42. Examples of the inert gas include nitrogen gas, helium gas, and the like. The gas supply section 45 is an example of a purge gas supply section. Gas supplied from the gas supply section 45 is an example of purge gas.

As described above, when the sample tube 2 is at the removal position (see FIG. 4D and FIG. 5D), the gear 44 rotates in one direction in the sample removing mechanism 40 (counterclockwise direction in FIG. 6).

This rotation of the gear 44 causes the shaft 41 (shaft section 411) to move in a direction toward the sample tube 2. When the gear 44 further rotates, the shaft 41 moves into the sample tube 2, so that the contact surface 412A of the contact section 412 of the shaft 41 comes into contact with the silica wool member 5 (the silica wool member 5 and the sample 6). Specifically, the contact section 412 is inserted into the sample tube 2 from a tapered portion of the contact section 412 (the contact surface 412A).

When the shaft 41 further moves into the sample tube 2, the contact surface 412A of the contact section 412 pushes out the silica wool members 5 and the sample 6 from the sample tube 2 (see FIG. 4E and FIG. 5E).

Then, the gear 44 rotates in the opposite direction (clockwise direction in FIG. 6).

This rotation of the gear 44 causes the shaft 41 to move in a direction away from the sample tube 2. When the gear 44 further rotates, the shaft 41 is pulled out from the sample tube 2. Then, the shaft 41 (a distal end of the shaft 41) is disposed in the heater block 42.

In this operation, the sample compound remaining in the sample tube 2 adheres to the shaft 41. In this example, the SVOC remains in the sample tube 2. Thus, when the shaft 41 is inserted in the sample tube 2, the SVOC adheres to the shaft 41. Specifically, in this process, the sample compound adheres to the contact surface 412A of the contact section 412 of the shaft 41.

When the shaft 41 is disposed in the heater block 42 after being pulled out from the sample tube 2, the heater block 42 heats the portion of the shaft 41 disposed in the heater block 42.

As a result, the sample compound adhered to the shaft 41 is diffused (dispersed).

The gas supply section 45 supplies gas (purge gas) into the heater block 42. The gas is blown onto the outer circumference surface of the shaft 41.

As a result, the sample compound diffused from the shaft 41 is moved (blown) away from the shaft 41. Due to the sealing between the end portion of the heater block 42 and the shaft section 411 of the shaft 41 in the heater block 42, the diffused sample compound flows out through the end portion of the heater block 42 facing the sample tube 2.

Thereafter, the operation described above is repeated each time the sample tube 2 is disposed at the removal position. At this point, the sample compound has been removed from the surface of the shaft 41, and thus the sample compound generated by the previous operation can be prevented from mixing into the sample tube 2, whereby occurrence of so-called cross contamination is prevented.

4. Operation and Effect (1) The sample introduction device 10 according to the present embodiment includes the sample removing mechanism 40. As illustrated in FIG. 4E, the sample removing mechanism 40 removes the sample 6 in the sample tube 2 held by the tube holding section 21.

Thus, in the sample introduction device 10, the sample 6 in the sample tube 2 held by the tube holding section 21 can be automatically removed.

As a result, the operator no longer needs to perform an operation of taking out the sample 6 from the sample tube 2.

Thus, a work load on the operator can be reduced. Furthermore, the time required for a series of processing in the sample introduction device 10 can be shortened.

(2) In the present embodiment, the sample removing mechanism 40 has the shaft 41 having a rod shape as illustrated in FIG. 6. The shaft 41 is inserted into the sample tube 2 to push out the sample 6 contained in the sample tube 2.

Thus, the sample in the sample tube 2 can be removed with a simple configuration.

(3) In the present embodiment, as illustrated in FIG. 5, in the sample removing mechanism 40, the shaft 41 includes the shaft section 411 and the contact section 412 attached to the distal end of the shaft section 411. The shaft section 411 is configured to be slidable in the axial direction. The contact section 412 has an outer diameter, about the axis, larger than the outer diameter of the shaft section 411.

Thus, when the shaft 41 is inserted in the sample tube 2, the contact section 412 comes into contact with the sample 6 and the silica wool member 5.

When the shaft 41 is further inserted into the sample tube 2, the contact section 412 pushes out the sample 6 (the sample 6 and the silica wool members 5) from the sample tube 2.

As a result, the portion of the sample removing mechanism 40 that comes into contact with the sample 6 in the process of removing the sample 6 can be limited to the contact section 412.

(4) In the present embodiment, the contact section 412 is detachably attached to the shaft section 411.

Thus, the contact section 412 can be exchanged and maintained easily.

(5) In the present embodiment, as illustrated in FIG. 6, the contact section 412 has the tapered surface 412B formed to be tapered toward the distal end.

Thus, when the contact section 412 is inserted into the sample tube 2, the contact section 412 is inserted into the sample tube 2 from the contact surface 412A that is a tapered portion.

This enables the contact section 412 to be easily inserted into the sample tube 2.

(6) In the present embodiment, as illustrated in FIG. 6, the sample removing mechanism 40 includes the heater block 42. The heater block 42 heats the shaft 41 that has been pulled out from the sample tube 2.

Thus, when the shaft 41 is inserted into the sample tube 2 and the sample compound remaining in the sample tube 2 adheres to the shaft 41, the heater block 42 heats the shaft 41, so that the adhered sample compound can be diffused (dispersed).

As a result, when the shaft 41 is continuously used, the shaft 41 with the sample compound adhered can be prevented from being inserted into the sample tube 2.

Thus, the occurrence of so-called cross contamination can be prevented, that is, the sample component adhered to the shaft 41 can be prevented from mixing into the sample tube 2 to adversely affect the subsequent analysis and the like.

(7) In the present embodiment, as illustrated in FIG. 6, the sample removing mechanism 40 includes the gas supply section 45. The gas supply section 45 blows the purge gas onto the outer circumference surface of the shaft 41 heated by the heater block 42.

With the purge gas thus blown onto the outer circumference surface of the shaft 41 from the gas supply section 45, the sample compound diffused from the surface of the shaft 41 can be moved (blown) away from the shaft 41 quickly.

As a result, the occurrence of the cross contamination can more effectively be prevented. Furthermore, the time required for removing the sample can be shortened, whereby the sample removing mechanism 40 can have a higher throughput.

(8) In the present embodiment, as illustrated in FIG. 5F, the sample introduction device 10 includes the sample detection section 50. The sample detection section 50 detects presence or absence of the sample 6 is in the sample tube 2 after the sample removing mechanism 40 has been operated.

Thus, whether or not the sample removing mechanism 40 has properly operated, that is, whether the sample 6 in the sample tube 2 has been pushed out can be confirmed based on the detection by the sample detection section 50.

5. Second Embodiment

A sample introduction device 10 according to a second embodiment of the present invention is described below with reference to FIG. 7. Components having the same configuration as those of the first embodiment are denoted with the same reference numerals, and the description thereof will be omitted.

Figure 7:
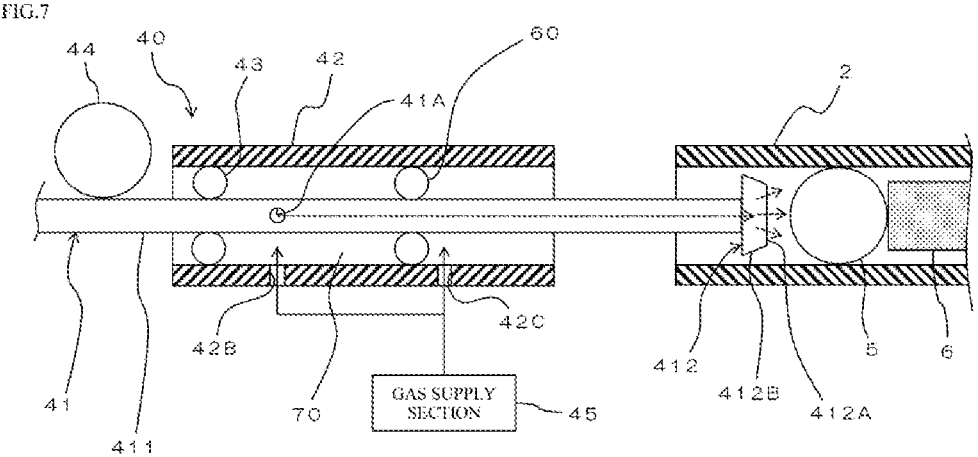
FIG. 7 is a schematic view illustrating a configuration of a sample removing mechanism of a sample introduction device according to a second embodiment of the present invention.

FIG. 7 is a schematic view illustrating a configuration of a sample removing mechanism 40 of the sample introduction device 10 according to the second embodiment of the present invention.

In the first embodiment described above, in the sample removing mechanism 40, the sample 6 in the sample tube 2 is removed with the contact section 412 of the shaft 41 coming into contact with and pushing out the sample 6 in the sample tube 2. On the other hand, in the second embodiment, the sample 6 is removed with the contact section 412 of the shaft 41 coming into contact and with the gas ejected from the shaft 41.

Specifically, in the second embodiment, the sample removing mechanism 40 further includes an O ring 60.

The O ring 60 is disposed at an inner position of the heater block 42. Specifically, the O ring 60 is disposed in the heater block 42 while being separated from the O ring 43 in the axial direction. The shaft section 411 of the shaft 41 is inserted in the O ring 60. Thus, the O ring 60 seals between the inner surface of the heater block 42 and the shaft section 411 of the shaft 41.

Thus, in the heater block 42, an internal space 70 is defined by the O ring 43, the O ring 60, and the outer circumference surface of the shaft section 411. Openings 42B and 42C are formed on the circumference surface of the heater block 42.

The opening 42B is provided between the O ring 43 and the O ring 60 in the axial direction, and the opening 42C is provided closer to the sample tube 2 than the O ring 60 is.

The gas supply section 45 supplies the gas into the heater block 42 through each of the openings 42B and 42C. The gas supplied into the heater block 42 through the opening 42B flows into the internal space 70. The gas supplied into the heater block 42 through the opening 42C is blown onto the outer circumference surface of the shaft 41 as the purge gas. In the second embodiment, the gas supply section 45 functions as a purge gas supply section and also functions as an extrusion gas supply section.

A through hole 41A is formed on the shaft 41. The through hole 41A is formed to pass through the shaft section 411 in the axial direction from a center portion to the distal end of the shaft section 411, and is also formed to pass through the inside of the contact section 412 in the axial direction. As illustrated in FIG. 7, the through hole 41A communicates with the internal space 70, with the contact section 412 of the shaft 41 positioned inside the sample tube 2.

The gas supplied from the gas supply section 45 into the internal space 70 of the heater block 42 through the opening 42B, passes through the through hole 41A to be ejected from the distal end of the contact section 412.

Thus, when the shaft 41 is inserted into the sample tube 2, the silica wool members 5 and the sample 6 can be pushed out from the sample tube 2 with the contact section 412 coming into contact and with the gas (extrusion gas) ejected from the contact section 412.

The shaft 41 may have the through hole 41A formed from one end (distal end) to the other end of the shaft section 411, and the gas from the gas supply section 45 may be supplied from the other end of the shaft section 411.

As described above, with the sample removing mechanism 40 of the sample introduction device 10 according to the second embodiment, the gas supply section 45 supplies the extrusion gas into the shaft 41 and the extrusion gas is ejected from the distal end of the contact section 412 of the shaft 41 toward the sample 6 in the sample tube 2.

Thus, when the shaft 41 is inserted into the sample tube 2, the extrusion gas ejected from the gas supply section 45 can push out the sample 6 in the sample tube 2.

As a result, the sample 6 in the sample tube 2 can be smoothly pushed out.

6. Modification

In the embodiments described above, the sample introduction device 10 is described as a sample introduction device for a gas chromatograph. However, the sample introduction device 10 can be used with other analysis devices.

In the embodiments described above, the sample removing mechanism 40 is configured to execute processing including both of; heating, by the heater block 42, the shaft 41 pulled out from the sample tube 2; and supplying the purge gas from the gas supply section 45. Alternatively, for example, only the heating by the heater block 42 may be performed. Still, when the processing including both of the heating and the purge gas supplying is executed on the shaft 41 as in the embodiments described above, the throughput of the sample removing mechanism 40 can be improved.

In the first embodiment described above, the sample 6 in the sample tube 2 is removed with the contact section 412 of the shaft 41 coming into contact with and pushing out the sample 6. In the second embodiment described above, the sample 6 is removed with the contact section 412 of the shaft 41 coming into contact and with the gas ejected from the shaft 41. However, the sample removing mechanism 40 may remove the sample 6 in the sample tube 2 with methods other than these. For example, the sample removing mechanism 40 may have a mechanism for tilting the sample tube 2, and the sample 6 may be discharged to the outside of the sample tube 2 by its own weight by causing the sample tube 2 to tilt by the mechanism.

Furthermore, the sample removing mechanism 40 may discharge the sample 6 from the sample tube 2 to the outside by means of the extrusion gas ejected from the shaft 41, without bringing the contact section 412 of the shaft 41 into contact with the sample 6. With this configuration, the sample compound can be prevented from adhering to the shaft 41, whereby the occurrence of the cross contamination can more effectively be prevented.

In the second embodiment described above, the gas (purge gas) supplied from the gas supply section 45 is partially supplied into the shaft 41 to be used as the extrusion gas. Alternatively, a gas supply section different from the gas supply section 45 may be provided, and the extrusion gas may be supplied into the shaft 41 from the gas supply section.

DESCRIPTION OF REFERENCE SIGNS 2 sample tube
6 sample
10 sample introduction device
21 tube holding section
4 sample removing mechanism
1 shaft
42 heater block
45 gas supply section
50 sample detection section
411 shaft section
412 contact section
412A contact surface
412B tapered surface

The invention claimed is:

1. A sample introduction device that heats a sample tube containing a sample to desorb a sample compound and introduce the sample compound into an analysis section, the sample introduction device comprising:
    a tube holding section that holds the sample tube;
    a sample removing mechanism that removes the sample in the sample tube held by the tube holding section, wherein the sample removing mechanism includes a shaft that is inserted into the sample tube to push out the sample; and
    a shaft heating section that heats the shaft that has been pulled out from the sample tube.

2. The sample introduction device according to claim 1, wherein the shaft includes a shaft section that slides in an axial direction and a contact section that has an outer diameter, about an axis, larger than an outer diameter of the shaft section, and comes into contact with the sample in the sample tube.

3. The sample introduction device according to claim 2, wherein the contact section is detachably attached to the shaft section.

4. The sample introduction device according to claim 2, wherein the contact section is provided with a tapered surface that is tapered toward a distal end.

5. The sample introduction device according to claim 1, further comprising a purge gas supply section that blows purge gas onto an outer circumference surface of the shaft heated by the shaft heating section.

6. The sample introduction device according to claim 1, wherein the shaft heating section is a heater block into which the shaft is pulled when the shaft is pulled out from the sample tube.

7. The sample introduction device according to claim 6, further comprising a gas supply section that supplies gas into the heater block through at least one opening in the heater block.

8. The sample introduction device according to claim 6, wherein the gas in the heater block is supplied to a through hole of the shaft to cause the gas to be ejected from a distal end of the shaft toward the sample in the sample tube.

9. The sample introduction device according to claim 1, further comprising a sample detection section that detects presence or absence of the sample in the sample tube after the sample removing mechanism has been operated.

10. A sample introduction device that heats a sample tube containing a sample to desorb a sample compound and introduce the sample compound into an analysis section, the sample introduction device comprising:
   a tube holding section that holds the sample tube;
   a sample removing mechanism that removes the sample in the sample tube held by the tube holding section, wherein the sample removing mechanism includes a shaft that is inserted into the sample tube to push out the sample, the shaft including a through hole; and
   an extrusion gas supply section that supplies extrusion gas into the through hole of the shaft to cause the extrusion gas to be ejected from a distal end of the shaft toward the sample in the sample tube.

* * * * *